United States Patent
Sugiyama

(10) Patent No.: US 9,671,419 B2
(45) Date of Patent: Jun. 6, 2017

(54) LIQUID COLLECTION DEVICE AND AUTOMATED ANALYZER PROVIDED THEREWITH

(71) Applicant: SHIMADZU CORPORATION, Kyoto-shi, Kyoto (JP)

(72) Inventor: Kiyohiro Sugiyama, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 15/103,504

(22) PCT Filed: Dec. 16, 2013

(86) PCT No.: PCT/JP2013/083555
§ 371 (c)(1),
(2) Date: Jun. 10, 2016

(87) PCT Pub. No.: WO2015/092844
PCT Pub. Date: Jun. 25, 2015

(65) Prior Publication Data
US 2016/0313362 A1    Oct. 27, 2016

(51) Int. Cl.
*G01N 35/10* (2006.01)
*G01N 35/00* (2006.01)
*G01N 35/02* (2006.01)

(52) U.S. Cl.
CPC ... *G01N 35/1016* (2013.01); *G01N 35/00722* (2013.01); *G01N 35/021* (2013.01);
(Continued)

(58) Field of Classification Search
CPC ... G01N 2035/1025; G01N 2035/1018; G01N 35/1016; G01N 2035/00326; G01N 2035/009
See application file for complete search history.

(56) References Cited

U.S. PATENT DOCUMENTS 4,228,831 A * 10/1980 Kerns ............... G01N 35/1009
141/27
4,818,492 A * 4/1989 Shimizu ............... G01F 23/263
422/509
(Continued)

FOREIGN PATENT DOCUMENTS

JP    2010-216956 A    9/2010
JP    5093164 B2    12/2012

OTHER PUBLICATIONS

International Search Report of PCT/JP2013/083555 dated Mar. 4, 2014 [PCT/ISA/210].

*Primary Examiner* — Brian R Gordon
(74) *Attorney, Agent, or Firm* — Sughrue Mion, PLLC

(57) ABSTRACT

A liquid collection device is configured to determine a difference between a liquid level after suction operation determined by calculation based on the liquid level detected at the time of previous probe lowering operation and a liquid level that is actually detected at the time of current probe lowering operation, to detect presence of foam if the difference is greater than a first threshold set as a maximum value of an allowable error set in advance in the device and is equal to or smaller than a second threshold that is set greater than the first threshold, and moreover, to display a warning to an operator when presence of foam is detected.

15 Claims, 11 Drawing Sheets

(52) U.S. Cl.
CPC ............ *G01N 2035/009* (2013.01); *G01N 2035/00326* (2013.01); *G01N 2035/1025* (2013.01)

(56) References Cited

U.S. PATENT DOCUMENTS

| | | | | |
|---|---|---|---|---|
| 5,777,221 A * | 7/1998 | Murthy | ............... | G01F 1/7086 250/577 |
| 5,866,426 A * | 2/1999 | Ball | ............... | G01F 23/265 340/620 |
| 5,919,706 A * | 7/1999 | Tajima | ............... | G01F 23/292 422/106 |
| 6,227,053 B1 * | 5/2001 | Purpura | ............... | G01F 23/296 73/290 V |
| 6,270,726 B1 * | 8/2001 | Tyberg | ............... | G01N 35/1011 422/509 |
| 6,322,752 B1 * | 11/2001 | Siddiqui | ............... | G01N 35/10 422/105 |
| 6,551,558 B1 * | 4/2003 | Mann | ............... | G01F 23/24 116/109 |
| 6,641,545 B1 * | 11/2003 | Colin | ............... | G01N 35/1016 600/573 |
| 6,740,529 B2 | 5/2004 | Takahashi | ............... | G01N 1/38 422/562 |
| 7,220,385 B2 * | 5/2007 | Blecka | ............... | G01N 35/0099 422/561 |
| 7,413,710 B2 * | 8/2008 | Lisec | ............... | B01L 3/022 422/417 |
| 7,439,076 B1 * | 10/2008 | Tokiwa | ............... | B01L 3/021 422/562 |
| 7,585,678 B2 * | 9/2009 | Sigrist | ............... | G01N 35/1011 422/430 |
| 7,670,564 B2 * | 3/2010 | Yoshida | ............... | G01F 23/292 222/113 |
| 7,998,751 B2 * | 8/2011 | Evers | ............... | B01F 11/0071 422/500 |
| 8,444,936 B2 * | 5/2013 | Taniguchi | ............... | G01N 35/1004 422/501 |
| 9,086,396 B2 * | 7/2015 | Burkard | ............... | G01N 35/1011 |
| 2004/0034479 A1 * | 2/2004 | Shimase | ............... | G01N 35/1016 702/19 |
| 2004/0101440 A1 * | 5/2004 | Ishizawa | ............... | G01N 35/1009 422/64 |
| 2004/0156417 A1 * | 8/2004 | Siddiqui | ............... | G01N 35/1011 374/45 |
| 2006/0093525 A1 * | 5/2006 | Brunner | ............... | G01F 23/2965 422/509 |
| 2006/0207322 A1 * | 9/2006 | Krufka | ............... | G01F 23/263 73/304 C |
| 2007/0020763 A1 * | 1/2007 | Ingenhoven | ............... | B01L 3/021 436/43 |
| 2009/0060785 A1 * | 3/2009 | Shimane | ............... | G01F 23/265 422/67 |
| 2009/0075386 A1 * | 3/2009 | Dunfee | ............... | G01N 35/1009 436/54 |
| 2009/0211380 A1 * | 8/2009 | Tajima | ............... | G01N 35/1016 73/864.11 |
| 2009/0226346 A1 * | 9/2009 | Miyato | ............... | G01N 21/11 422/400 |
| 2009/0266149 A1 * | 10/2009 | Kaplit | ............... | G01N 35/1016 73/54.09 |
| 2012/0114526 A1 * | 5/2012 | Watanabe | ............... | G01F 23/00 422/63 |
| 2013/0121880 A1 * | 5/2013 | Yamazaki | ............... | G01N 35/1016 422/81 |
| 2014/0190253 A1 * | 7/2014 | Nishida | ............... | G01N 35/1011 73/304 C |
| 2015/0219680 A1 * | 8/2015 | Mimura | ............... | G01N 35/1016 436/43 |
| 2015/0268230 A1 * | 9/2015 | Endo | ............... | G01F 23/00 422/69 |
| 2015/0323557 A1 * | 11/2015 | Tamezane | ............... | G01N 35/1009 422/67 |

\* cited by examiner

LIQUID COLLECTION DEVICE AND AUTOMATED ANALYZER PROVIDED THEREWITH

CROSS REFERENCE TO RELATED APPLICATIONS

This application is a National Stage of International Application No. PCT/JP2013/083555, filed Dec. 16, 2013, the contents of which are incorporated herein by reference in its entirety.

TECHNICAL FIELD

The present invention relates to a liquid collection device for collecting a liquid contained in a container through a probe, and an automated analyzer provided with the liquid collection device.

BACKGROUND ART

As an example, an automated analyzer automatically performs a series of operations of dispensing a predetermined amount of specimen into a reaction vessel, adding a predetermined amount of reagent to the specimen, and then optically measuring the reaction in the reaction vessel by a predetermined measurement section. Various reagents to be added to a specimen are placed by an operator in a predetermined reagent accommodating section of the device, and information about the placed reagents and the placement positions are associated and registered with the device.

Tasks of collecting a specimen from a specimen container and dispensing the specimen into a reaction vessel and of collecting a reagent placed in a reagent accommodating section and dispensing the reagent into the reaction vessel are generally performed by an automated analyzer as described above by using a probe that performs suction and discharge of liquid. In this case, the probe is arranged above a container containing a target specimen or reagent, is lowered to have its tip end placed inside the container to suck in the liquid, and the liquid sucked in is dispensed into the reaction vessel by moving the probe to the position of the reaction vessel.

The automated analyzer described above is sometimes provided with a liquid level sensor for detecting the tip end of the probe coming into contact with the liquid surface, with the aim of preventing pollution of the probe due to the probe being dipped into a specimen or a reagent more than necessary at the time of suction of the specimen or the reagent by the probe (for example, see Patent Document 1). In this case, the outer surface of the probe may be prevented from being polluted by the specimen or the reagent more than necessary, by lowering the probe from above a suction target liquid and detecting the position of the probe at the time of the probe tip end coming into contact with the liquid, and by sucking in the liquid by lowering the probe from the position by only a necessary distance.

Furthermore, the liquid level inside the container may be determined by detecting, by the liquid level sensor, the height of the probe at the time of the probe tip end coming into contact with the liquid, and thus, a function of automatically recognizing the remaining amount of a suction target liquid may be realized.

PRIOR ART DOCUMENTS

Patent Documents

Patent Document 1: Japanese Patent No. 5093164

SUMMARY OF THE INVENTION

Problems to be Solved by the Invention

As a specimen for the automated analyzer, serum and the like may be cited, and in many cases, a reagent to be added to such a specimen includes a surface active agent, and foam tends to be generated on the liquid surface of such a reagent. However, a liquid level sensor provided to the device detects contact of the probe tip end with the foam in the same manner as contact with the liquid surface, and it is not possible to distinguish between whether the liquid level sensor has detected the liquid surface of a reagent or the foam. Accordingly, in the case where foam is generated on the liquid surface of a reagent, if the probe tip end comes into contact with the foam and this is detected by the liquid level sensor, suction operation for the reagent is performed with reference to the position, and a predetermined amount of reagent is not sucked in, and the reliability of an analysis result for a specimen added with the reagent is reduced. Moreover, even when the reliability of an analysis result is reduced due to the foam on the liquid surface of a reagent, it is difficult for an operator to recognize the reduction in reliability.

It is conceivable to add a pressure sensor in addition to the liquid level sensor, and to detect a subtle change in the pressure on the probe, so as to determine whether the probe tip end has come into contact with the liquid surface or the foam. However, there are problems that, since a pressure sensor has to be added separately from the liquid level sensor, the device cost is increased, and also that, because a subtle change in pressure has to be detected with high accuracy, adjustment of the sensor is difficult.

Accordingly, the present invention has its aim to enable detection of foam generated on the liquid surface of a suction target by using a liquid level sensor, without addition of a new sensor.

Solutions to the Problems

A liquid collection device according to the present invention includes a probe, a probe driving mechanism, a pump, a liquid level sensor, probe operation control means, liquid level detection means, post-suction liquid level calculation means, a post-suction liquid level storage section, a first threshold holding section, a second threshold holding section, difference calculation means, foam detection means, and warning display means.

The liquid level sensor is for detecting that a tip end of the probe has come into contact with a liquid surface. The probe driving mechanism is for driving the probe in at least a vertical direction, and the probe operation control means is for controlling the probe driving mechanism and the pump so as to perform a probe lowering operation and a suction operation. The liquid level detection means is configured to detect a liquid level before the suction operation by detecting a position of the probe at a time of the probe tip end coming into contact with the liquid surface at a time of the probe lowering operation. The post-suction liquid level calculation means is configured to calculate a theoretical value of the liquid level after the suction operation based on the liquid level before the suction operation detected by the liquid level detection means and an amount of suction at a time of the suction operation, and the post-suction liquid level storage section is for storing the theoretical value of the liquid level.

The first threshold holding section holds a first threshold that is set in advance, and the second threshold holding section holds a second threshold that is set in advance. The first threshold is a maximum value of an error allowed for a difference between the theoretical value of the liquid level after the suction operation calculated by the post-suction liquid level calculation means and an actual liquid level after the suction operation. The second threshold is set greater than the first threshold.

The difference calculation means is configured to calculate, when the probe lowering operation is to be performed for a second or subsequent time for a container of a same suction target, a difference between the liquid level detected by the liquid level detection means and the theoretical value, for the container, of the liquid level after the suction operation stored in the post-suction liquid level storage section. The foam detection means is configured to compare a difference value calculated by the difference calculation means against the first threshold and the second threshold, and to detect presence of foam if the difference value is greater than the first threshold and is equal to or smaller than the second threshold, and the warning display means is configured to output to an effect that presence of foam is detected by the foam detection means, at a time of the detection, by a method allowing recognition by an operator.

That is, the liquid collection device of the present invention is configured to determine the difference between the liquid level after suction operation determined by calculation based on the liquid level detected at the time of previous probe lowering operation and the liquid level that is actually detected at the time of current probe lowering operation, to detect presence of foam if the difference is greater than the first threshold that is set as a maximum value of an allowable error set in advance in the device and is equal to or smaller than the second threshold that is set greater than the first threshold, and moreover, to display a warning to an operator when presence of foam is detected.

If the second threshold is set smaller than the maximum value of the size of foam that may be generated on the liquid surface in a container, generation of foam is possibly not detected even when there is generation of foam. Further, if the second threshold is set greatly exceeding the maximum value of the size of foam that may be generated on the liquid surface inside the container, generation of foam may be recognized even when a reagent container which is a suction target was replaced by a new reagent container, or a reagent was replenished by an operator, for example. Therefore, a value that is extremely smaller or greater than the maximum value of the size of foam that may be generated is not desirable as the second threshold. Accordingly, the second threshold is preferably set based on the maximum value of the size of foam that may be generated on the liquid surface in a container.

Preferably, there is further included threshold selection means for selecting, in a case where a plurality of containers containing suction target liquids of the probe are provided, and the second threshold is individually set for each type of the suction target liquid, the second threshold according to the type of suction target liquid, and the foam detection means is configured to detect presence of foam by using the second threshold selected by the threshold selection means. This is because the size of foam that is generated on the liquid surface of a suction target liquid possibly varies depending on the type (property) of the liquid.

Further, preferably, there is further included threshold selection means for selecting, in a case where a plurality of containers containing suction target liquids of the probe are provided, and the second threshold is individually set for each size or shape of the container containing the suction target liquid, the second threshold according to the size or the shape of the container containing a suction target liquid, and the foam detection means is configured to detect presence of foam by using the second threshold selected by the threshold selection means. This is because the size of foam that is generated on the liquid surface of a suction target liquid possibly varies depending on the size or the shape of the container containing the liquid.

In a case where a plurality of containers containing suction target liquids of the probe are provided, the first threshold is also preferably individually set for each size or shape of the container containing the suction target liquid. This is because the error in the liquid level after suction based on the suction accuracy of the pump varies depending also on the size or the shape of the container. In this case, threshold selection means for selecting the first threshold according to the size or the shape of the container containing the suction target liquid is further included, and the foam detection means is configured to detect presence of foam by using the first threshold selected by the threshold selection means.

Furthermore, the foam detection means is preferably configured to detect, when the difference value calculated by the difference calculation means is greater than the second threshold, that the container containing the suction target liquid is a new container. Then, for example, if the reagent container is replaced by a new one, or the reagent is replenished, this may be automatically recognized by the device.

An example of a preferred mode of the liquid collection device of the present invention further includes an arithmetic control device including the probe operation control means, the liquid level detection means, the post-suction liquid level calculation means, the post-suction liquid level storage section, the threshold holding sections, the difference calculation means and the foam detection means, and an information display section, connected to the arithmetic control device, for displaying information held by the arithmetic control device, where the warning display means is configured to display on the information display section that presence of foam is detected by the foam detection means, at a time of the detection.

An automated analyzer according to the present invention includes a specimen collection mechanism for collecting a specimen from a specimen container containing the specimen, and dispensing the specimen into a reaction vessel for causing reaction of the specimen, a reagent dispensing mechanism, configured by a liquid collection device of the present invention, for sucking in a reagent from a reagent container containing the reagent, and dispensing the reagent into the reaction vessel, and a measurement section for performing measurement inside the reaction vessel containing the specimen and the reagent.

According to an example of a preferred mode of the automated analyzer of the present invention, a plurality of analyzers, each including the specimen collection mechanism, the reagent dispensing mechanism, and the measurement section are provided, and each of the analyzers includes a belt conveyor for conveying a specimen rack holding a plurality of specimen containers in one direction, and analyzers that are disposed adjacent to each other are disposed with an end of a belt conveyor of one of the analyzers and a beginning of a belt conveyor of an other of the analyzers facing each other, and the belt conveyors are linked together by an inter-device transport device including a transport mechanism for holding the specimen rack that reached the end of the belt conveyor of the one analyzer and transporting the specimen rack to the beginning of the belt conveyor of the other analyzer.

Effects of the Invention

The liquid collection device of the present invention is configured to determine the difference between the liquid level after suction operation determined by calculation based on the liquid level detected at the time of previous probe lowering operation and the liquid level that is actually detected at the time of current probe lowering operation, and to detect presence of foam if the difference is greater than the first threshold that is set as a maximum value of an allowable error set in advance in the device and is equal to or smaller than the second threshold that is set greater than the first threshold, and thus, foam generated on the liquid surface may be detected without provision of an additional sensor such as a pressure sensor. Moreover, since a warning is displayed to an operator when presence of foam is detected, the operator may easily recognize generation of foam on the liquid surface.

According to the automated analyzer of the present invention, the reagent dispensing mechanism is configured by the liquid collection device of the present invention, and thus, in a case where foam is generated on the liquid surface inside a reagent container containing a reagent to be added to a specimen, this may be detected, and the operator may easily recognize generation of foam.

EMBODIMENTS OF THE INVENTION

First Embodiment

An embodiment of a liquid collection device will be described.

Figure 1:
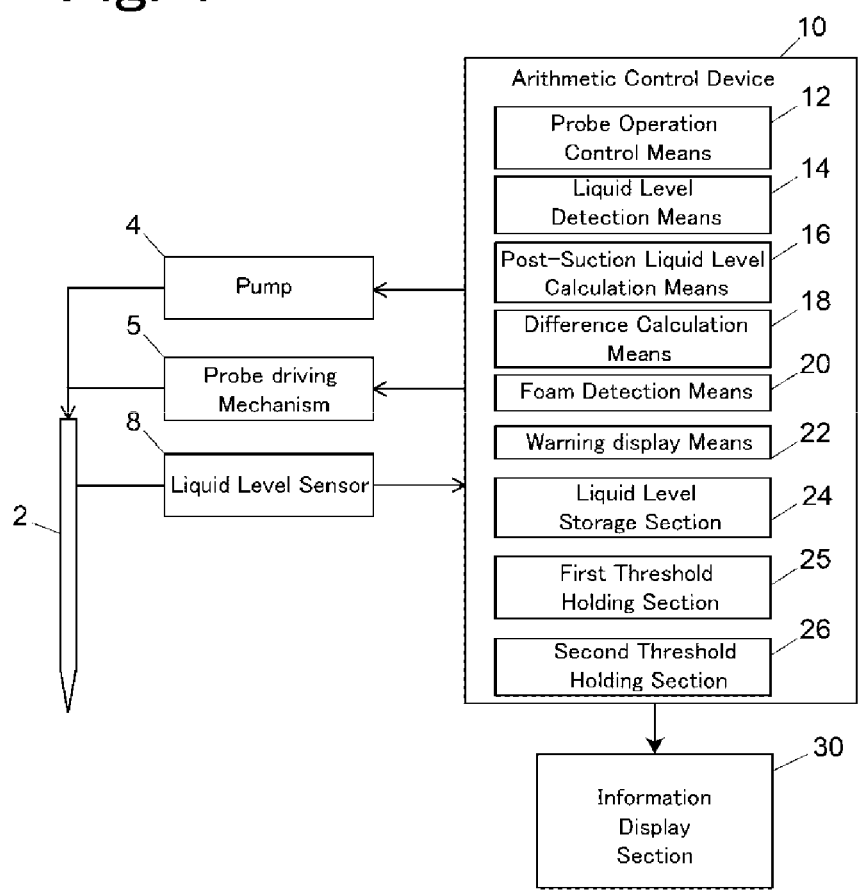
FIG. 1 is a schematic configuration diagram showing an embodiment of a liquid collection device.

As shown in FIG. 1, the liquid collection device includes a probe 2, a pump 4, a probe driving mechanism 5, a liquid level sensor 8, an arithmetic control device 10, and an information display section 30. The pump 4 is, for example, a syringe pump, and performs suction and discharge of a liquid through the probe 2. The probe driving mechanism 5 drives the probe 2 in a horizontal plane direction and a vertical direction. The liquid level sensor 8 is a capacitive sensor, and detects contact of a tip end of the probe 2 with a liquid surface by detecting a change in the capacitance when the tip end of the probe 2 comes into contact with the liquid surface.

Figure 2:
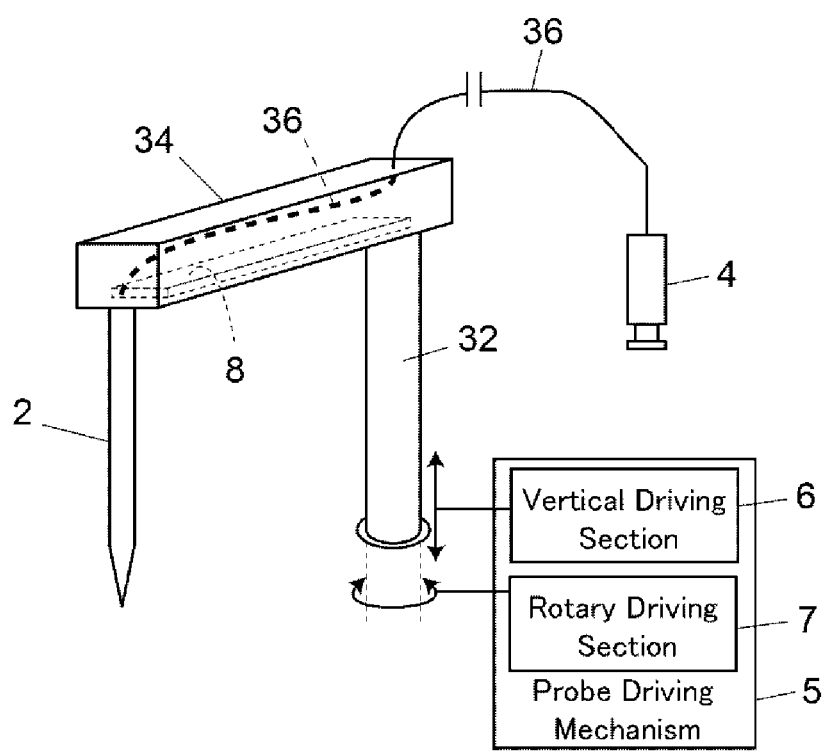
FIG. 2 is a diagram schematically showing mechanisms around a probe of the present embodiment.

As shown in FIG. 2, the tip end of the probe 2 is held at a tip end portion of an arm 34 in a vertical downward state. A base end portion of the arm 34 is supported by a support shaft 32 which is vertically disposed, and a tip end of the arm 34 extends in a horizontal direction. The support shaft 32 is capable of performing rotation on the horizontal plane and vertical movement in the vertical direction by a vertical driving section 6 and a rotary driving section 7 forming the probe driving mechanism 5, and thus is capable of moving the probe 2 held by the arm 34 in an arc in the horizontal plane direction, and of vertically moving the probe 2 at a position on the path. The vertical driving section 6 and the rotary driving section 7 each include a pulse motor as an element, and is capable of controlling the position of the probe 2 by the number of pulses applied to the pulse motor. A base end of the probe 2 is connected to the syringe pump 4 through a tube 36.

A sensor board 8 (the liquid level sensor) is provided inside the arm 34. The sensor board 8 detects a change in the capacitance between the tip end of the probe 2 and a liquid surface when the tip end of the probe 2 comes into contact with the liquid surface.

Referring back to FIG. 1, the arithmetic control device 10 is for performing various arithmetic processes based on detection signals from the liquid level sensor 8, in addition to performing operation control of the pump 4 and the probe driving mechanism 5. The information display section 30 is for displaying information held by the arithmetic control device 10. The arithmetic control device 10 is realized by a general-purpose personal computer (PC) or a dedicated computer, for example. The information display section 30 is realized by, for example, a general-purpose PC monitor or a dedicated monitor.

The arithmetic control device 10 includes probe operation control means 12, liquid level detection means 14, post-suction liquid level calculation means 16, difference calculation means 18, foam detection means 20, warning display means 22, a liquid level storage section 24, a first threshold holding section 25, and a second threshold holding section 26. Each of the probe operation control means 12, the liquid level detection means 14, the post-suction liquid level calculation means 16, the difference calculation means 18, the foam detection means 20, and the warning display means 22 is a function realized by a program installed in the arithmetic control device 10 and an arithmetic unit (CPU) for executing the program. The liquid level storage section 24, the first threshold holding section 25, and the second threshold holding section 26 are realized by a hard disk or a non-volatile memory provided to the arithmetic control device 10.

The probe operation control means 12 is configured to control the pump 4 and the probe driving mechanism 5 so as to perform, based on a dispensing condition specified by an operator regarding a suction target liquid, a probe lowering operation of lowering the probe 2 from a position above a container containing a target liquid, a suction operation of sucking in the liquid inside the container by a preset amount, and a dispensing operation of dispensing the sucked-in liquid into a predetermined dispensing position. The probe lowering operation is performed based on a detection signal of the liquid level sensor 8, and the probe 2 is made to stop at a position lower by a predetermined distance from the level of contact of the tip end of the probe 2 with the liquid surface. The suction operation is performed at the position.

The liquid level detection means 14 is configured to determine, at the time of the probe lowering operation, the height of the probe 2 at the time of the tip end of the probe 2 coming into contact with the liquid surface, based on a detection signal of the liquid level sensor 8, from the number of pulses applied to the pulse motor of the probe driving mechanism 5, for example, and to thereby detect a liquid level $H_1$ in the container. The liquid level $H_1$ which is detected at this time is the liquid level before the suction operation is performed. The detected liquid level $H_1$ is stored in the liquid level storage section 24.

The post-suction liquid level calculation means 18 is configured to calculate a liquid level $H_0$ after the suction operation by using the liquid level $H_1$ before the execution of the suction operation detected by the liquid level detection means 14, the liquid level $H_0$ being obtained by subtracting a height corresponding to the amount of suction of the liquid from the liquid level $H_1$. The liquid level $H_0$ calculated by the post-suction liquid level calculation means 18 is not the actual liquid level after suction, but is a theoretical value of the liquid level determined by calculation based on a suction condition. The calculated theoretical value $H_0$ of the liquid level is also stored in the liquid level storage section 24. The theoretical value $H_0$ is used after the next probe lowering operation for the same container to calculate a difference $\Delta H$ by the difference calculation means 18.

The difference calculation means 18 is configured to calculate, when the liquid level $H_1$ in a container is detected by the liquid level detection means 14, a difference $\Delta H$ $(=H_1-H_0)$ between the theoretical value $H_0$ calculated by the post-suction liquid level calculation means 18 at the time of previous liquid collection from the same container and the currently detected liquid level $H_1$.

The foam detection means 20 is configured to detect whether foam is generated on the liquid surface in the suction target container, by using the difference $\Delta H$ calculated by the difference calculation means 18 and based on the first threshold held by the first threshold holding section 25 and the second threshold held by the second threshold holding section 26.

The liquid level $H_1$ detected by the liquid level detection means 14 can be said to be the actual measurement value of the liquid level after the previous liquid suction. Because $H_0$ is a theoretical value of the liquid level after the previous suction operation determined by calculation, if the liquid level in the container is properly detected by the liquid level sensor 8, it should appear as $H_1 \approx H_0$. The threshold used to determine whether it appears as $H_1 \approx H_0$ or not by using the difference $\Delta H$ $(=H_1-H_0)$ is the first threshold. The first threshold is set taking into account an error in the amount of suction based on the suction accuracy of the pump 4.

A case where the liquid surface in a container is not properly detected by the liquid level sensor 8 is a case where foam is generated on the liquid surface and the foam is detected by the liquid level sensor 8 as the liquid surface when it comes into contact with the tip end of the probe 2. In this case, it always appears as $H_1 > H_0$, and $\Delta H$ exceeds the first threshold. In the case where the liquid surface is properly detected by the liquid level sensor 8, the difference $\Delta H$ $(=H_1-H_0)$ may take a positive value or a negative value, and thus, the first threshold may be set between $-\alpha$ and $+\alpha$, but since it always appears as $H_1 > H_0$ when foam is detected by the liquid level sensor 8, it is enough if the first threshold is set on the positive side only. In the present embodiment, the first threshold is set only on the positive side. When the first threshold is exceeded by the difference $\Delta H$ calculated by the difference calculation means 18, generation of foam on the liquid surface in the container is suspected.

As the case where the first threshold is exceeded by $\Delta H$, a case where the container was replaced by a new container (filled with liquid) after the previous liquid collection, and a case where the liquid inside the container was replenished are conceivable. The second threshold is a threshold for determining, when the first threshold is exceeded by $\Delta H$, whether this is due to foam generated on the liquid surface or to an increase in the amount of liquid. The second threshold takes into account the maximum value of the size of foam that is possibly generated on the liquid surface in the container. Accordingly, in the case where the second threshold is exceeded by $\Delta H$, it can be determined that the container was replaced by a new container or that the liquid was replenished.

The bubble detection means 20 is configured to compare, when the liquid level $H_1$ in the container is detected by the liquid level detection means 16, the $H_1$ and theoretical value $H_0$, and performs the following determination based on whether the first threshold is exceeded by the difference $\Delta H$ and whether the second threshold is exceeded by the $\Delta H$.

$\Delta H \leq 0 (H_1 \leq H_0)$      Normal

First threshold<$\Delta H \leq$second threshold . . . Foam is generated on the liquid surface Second threshold<$\Delta H$ . . . Suction target container is replaced by a new container The warning display means 22 is configured to output, to the information display section 30, to the effect that generation of foam on the liquid surface is detected by the bubble detection means 20, at the time of the detection. When display to that effect is performed on the information display section 30, this may be recognized by the operator.

Figure 3:
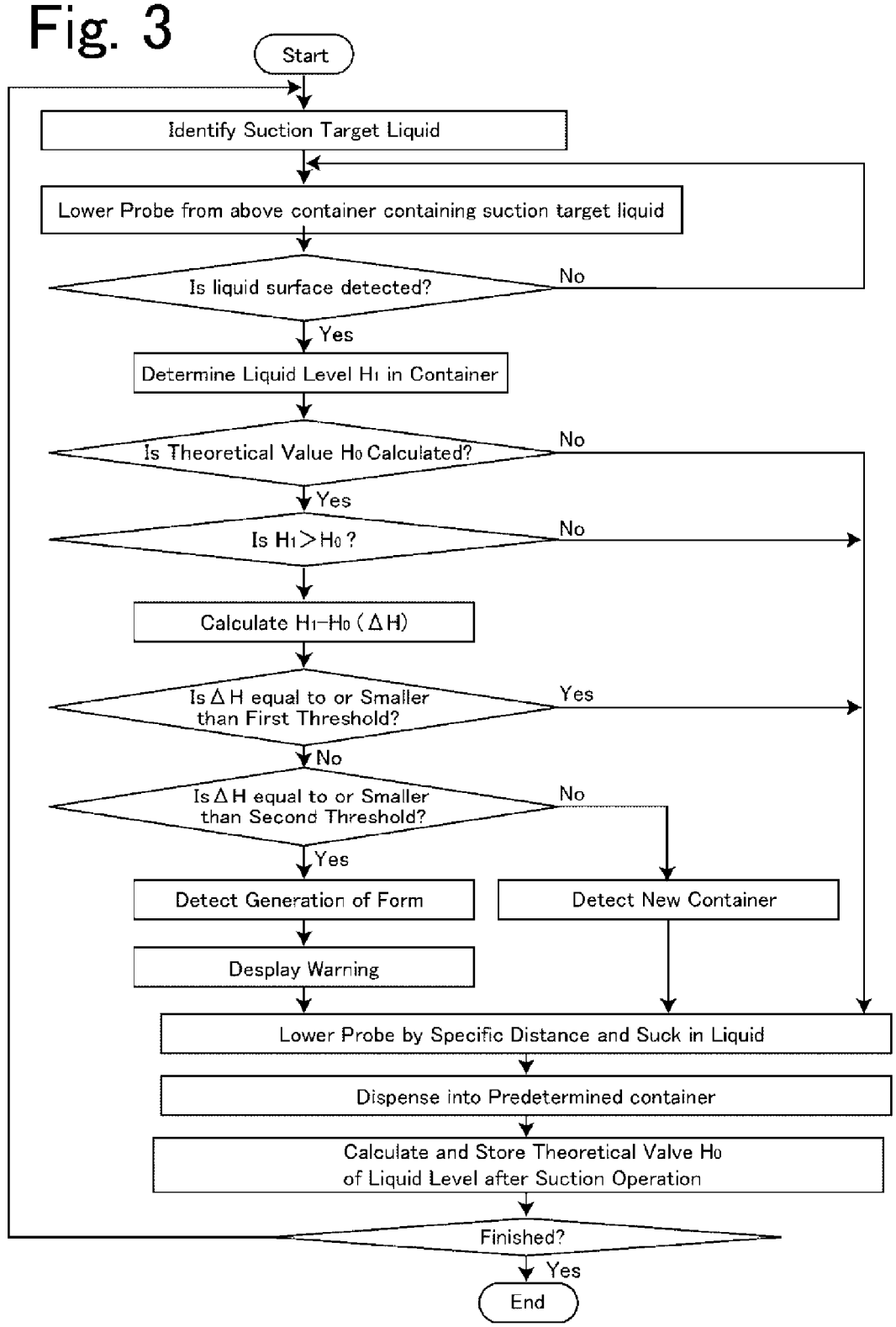
FIG. 3 is a flow chart showing liquid collection/dispensing operations of the present embodiment.

Next, a liquid collection operation of the present embodiment will be described with reference to FIG. 1 and the flow chart in FIG. 3.

Suction target liquids of the liquid collection device are, for example, a plurality of types of reagents placed in the automated analyzer. There are several liquids which may be the suction target, and each is placed contained in a separate container. When conditions regarding the type of liquid to be collected, the quantity, and the like are specified by the operator, the suction target liquid (container thereof) is identified based on the conditions, and the probe 2 is lowered from a position above the container until the liquid level sensor 8 detects the liquid surface (the probe lowering operation).

When the liquid surface is detected by the liquid level sensor 8, the probe 2 is stopped, and the liquid level $H_1$ in the suction target container is determined based on the position of the probe 2 at this time. In the case where the theoretical value $H_0$ of the liquid level after the previous suction operation for the same container is stored in the liquid level storage section 24, $H_1$ and $H_0$ are compared with each other, and if $H_1 \leq H_0$, normality is determined, and the probe 2 is further lowered by a specific distance and the liquid suction operation is performed. In the case where the theoretical value $H_0$ for the container is not stored in the liquid level storage section 24, the liquid collection operation is performed for the first time for the container, normality is determined, the probe 2 is further lowered by a specific distance and a predetermined amount of liquid is sucked in (suction operation), and the liquid is dispensed into a predetermined container (dispensing position) (the dispensing operation).

In the case of $H_1 > H_0$, the difference calculation means 18 calculates the difference $\Delta H$ ($=H_1-H_0$), and if $\Delta H$ is equal to or smaller than the first threshold, normality is determined. The probe 2 is then further lowered by a specific distance and the liquid suction operation is performed. If $\Delta H$ is greater than the first threshold, $\Delta H$ is compared with the second threshold, and if $\Delta H$ is equal to or smaller than the second threshold, it is determined that foam is generated on the liquid surface. In this case, output to that effect is performed on the information display section 30, and then, later suction operation and dispensing operation are performed. In the case where the liquid collection device is built in the automated analyzer, a warning to the effect that foam was possibly generated inside the container may be displayed at the time of display, on the information display section 30, of the result of analysis performed using the liquid collected by the suction operation. This allows the operator to recognize that the reliability of the analysis result is doubtful.

Furthermore, in another mode, when foam on the liquid surface is detected by the foam detection means 20, a warning to this effect may be displayed, and later suction operation and dispensing operation may be suspended until a check is performed by the operator.

In the case where the second threshold is exceeded by $\Delta H$, the container is determined to be a new container, and later suction operation and dispensing operation are performed. Further, in the case where the second threshold is exceeded by $\Delta H$, display may be performed on the information display section 30 to the effect that the container is a new container.

The theoretical value $H_0$ of the liquid level after the current suction operation is calculated based on the liquid level $H_1$ detected at the time of the probe lowering operation and the condition regarding the amount of suction. In FIG. 3, $H_0$ is calculated after the liquid dispensing operation, but the timing of calculation may be any timing as long as calculation of $H_0$ is possible.

Second Embodiment

Figure 4:
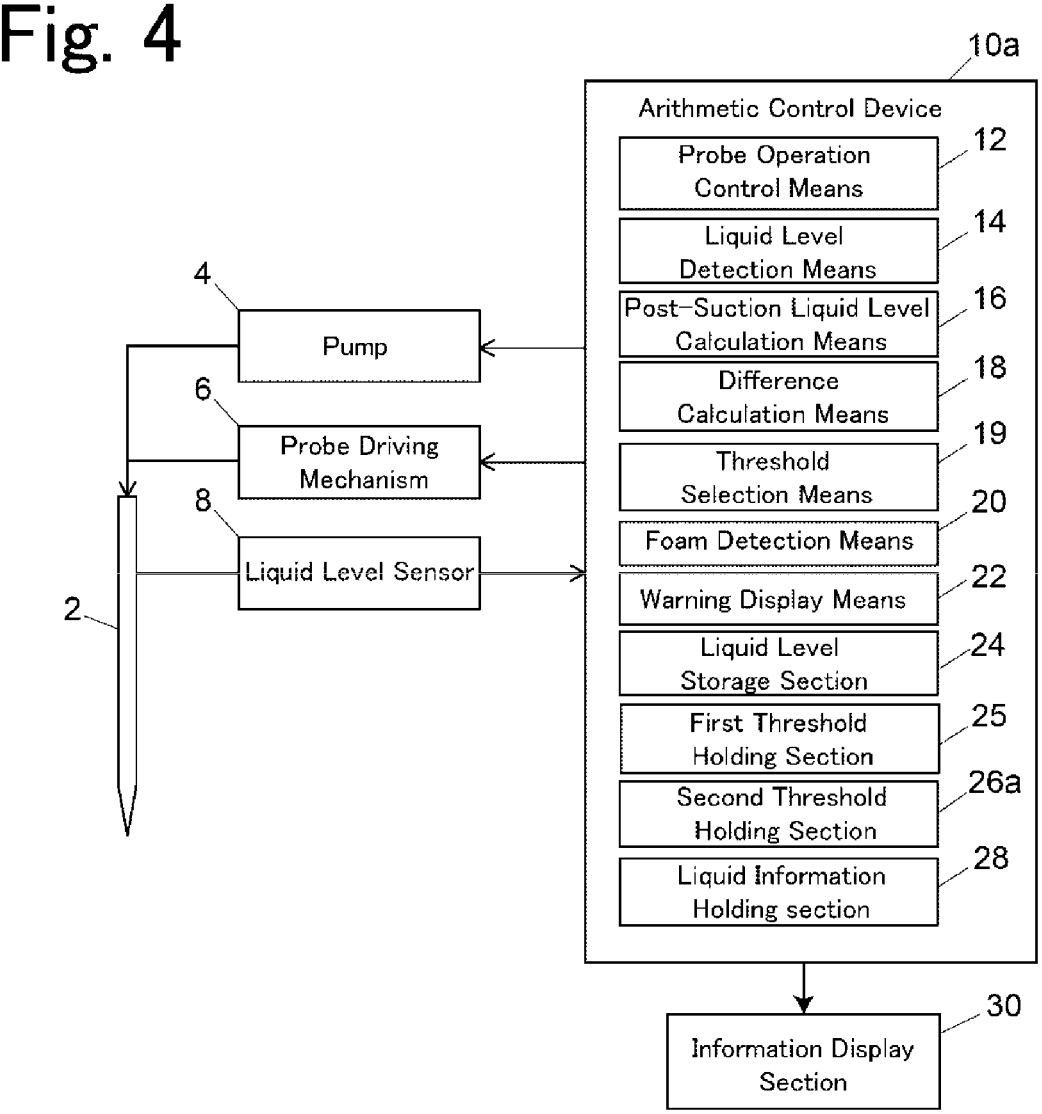
FIG. 4 is a schematic configuration diagram showing another embodiment of the liquid collection device.

Another embodiment of the liquid collection device will be described with reference to FIG. 4.

With the liquid collection device according to the present embodiment, the function of an arithmetic control device 10a for controlling operation of the pump 4 and the probe driving mechanism 6 is different from the function of the arithmetic control device 10 of the first embodiment described with reference to FIGS. 1 to 3, and other structures are the same as those in the first embodiment.

The arithmetic control device 10a of the present embodiment includes, in addition to the function of the arithmetic control device 10 of the first embodiment, threshold selection means 19 and a liquid information storage section 28. Moreover, the first threshold holding section 25 and the second threshold holding section 26 according to the first embodiment each hold a single value as the first threshold or the second threshold, but a first threshold holding section 25a and a second threshold holding section 26a according to the present embodiment each hold a plurality of values as the first threshold or the second threshold.

The size of foam that is generated on the liquid surface in a suction target container may vary depending on the type of the liquid, or the size or the shape of the container. Further, the range of allowable error in the liquid level after suction based on the suction accuracy of the pump 4 varies depending on the size or the shape of the container. Accordingly, thresholds according to the sizes and shapes of containers containing suction target liquids are held by the first threshold holding section 25a as the first thresholds. Thresholds according to the types of suction target liquids, or the sizes or the shapes of the containers are held by the second threshold holding section 26a as the second thresholds. The types of liquids and the sizes or the shapes of the containers are registered with the device in advance as liquid information, and are registered with the liquid information holding section 28.

The threshold selection means 19 is configured to read information about a suction target liquid identified based on a condition specified by the operator from the liquid information holding section 28, and to select the first threshold according to the size or the shape of the container containing the liquid from the first threshold holding section 25a, and to select the second threshold according to the type of the liquid and the size or the shape of the container from the second threshold holding section 26a. The foam detection means 20 performs detection of foam generated on the liquid surface by using the first threshold and the second threshold selected by the threshold selection means 19.

Figure 5:
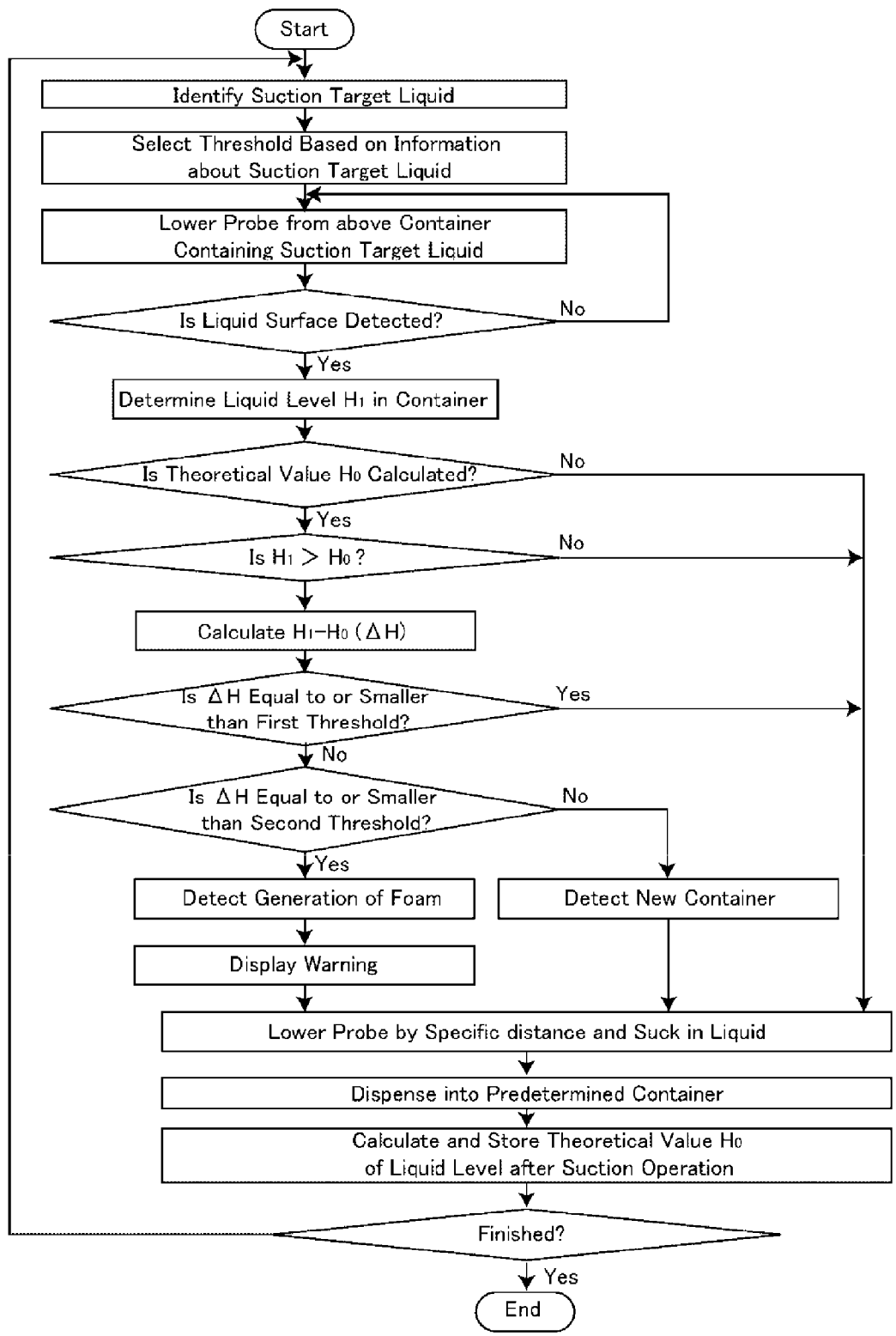
FIG. 5 is a flow chart showing liquid collection/dispensing operations of the present embodiment.

Operation according to the present embodiment will be described with reference to FIG. 4 and the flow chart in FIG. 5.

When conditions regarding the type of the liquid to be collected, the quantity, and the like are specified by the operator, the suction target liquid (container thereof) is identified based on the conditions, and information about the liquid is read from the liquid information holding section 28. The first threshold and the second threshold are selected based on the type of the liquid and the size or the shape of the container which have been read. The first threshold and the second threshold which are selected at this time are used for detection of foam in the suction target container. A series of processes from the subsequent probe lowering operation to the dispensing operation is the same as that in the first embodiment, and detailed description thereof is omitted.

Third Embodiment

Figure 6:
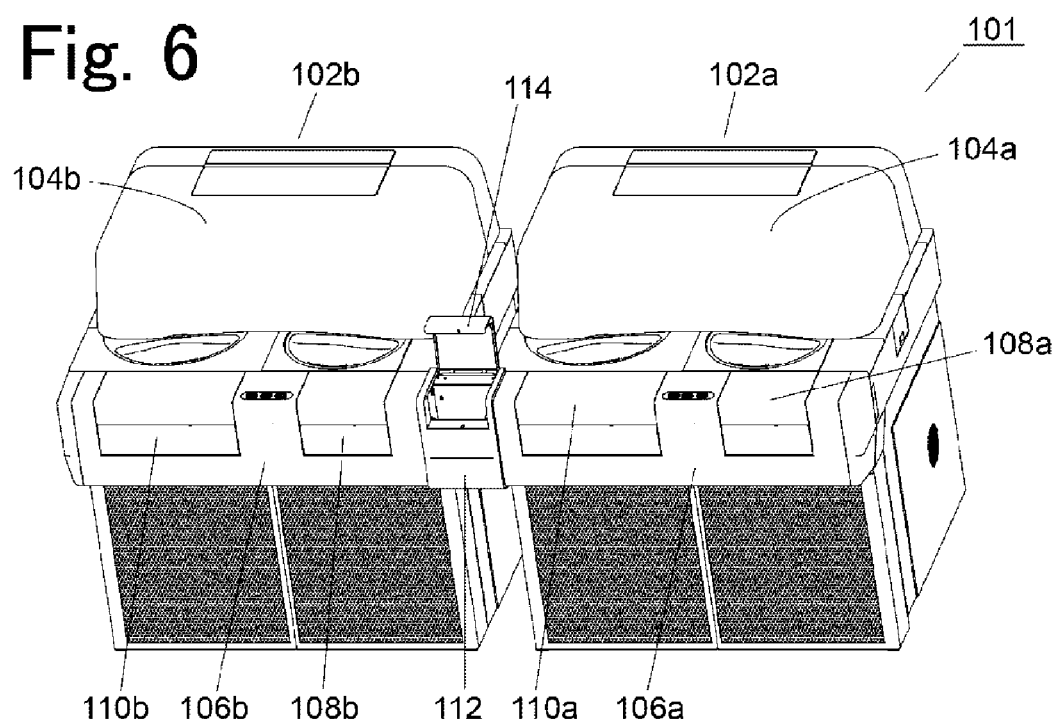
FIG. 6 is a schematic configuration diagram showing an embodiment of an automated analyzer.
Figure 7:
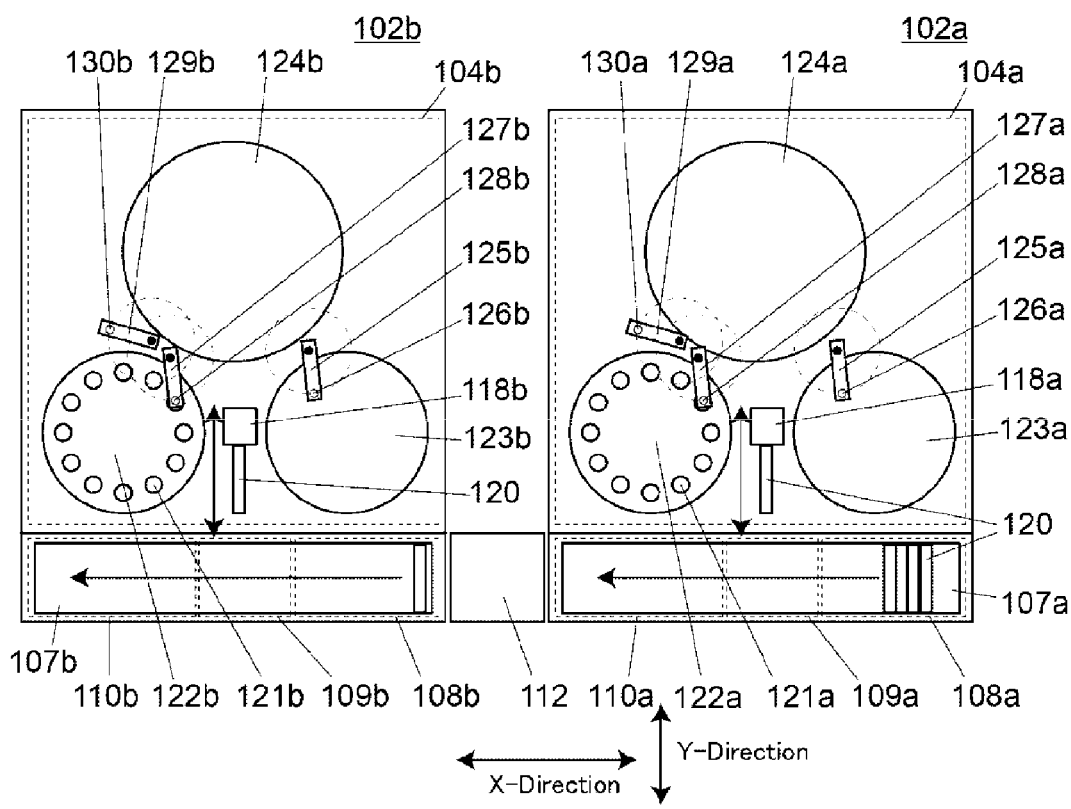
FIG. 7 is a plan view schematically showing a configuration of the present embodiment.
Figure 8:
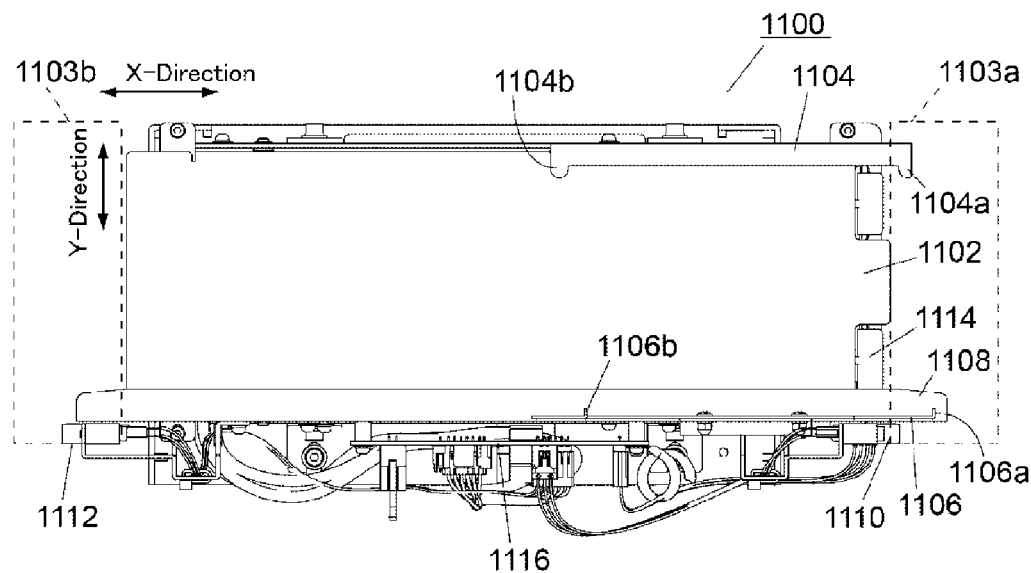
FIG. 8 is a plan view showing a transport mechanism of an inter-device transport device according to the present embodiment.
Figure 9:
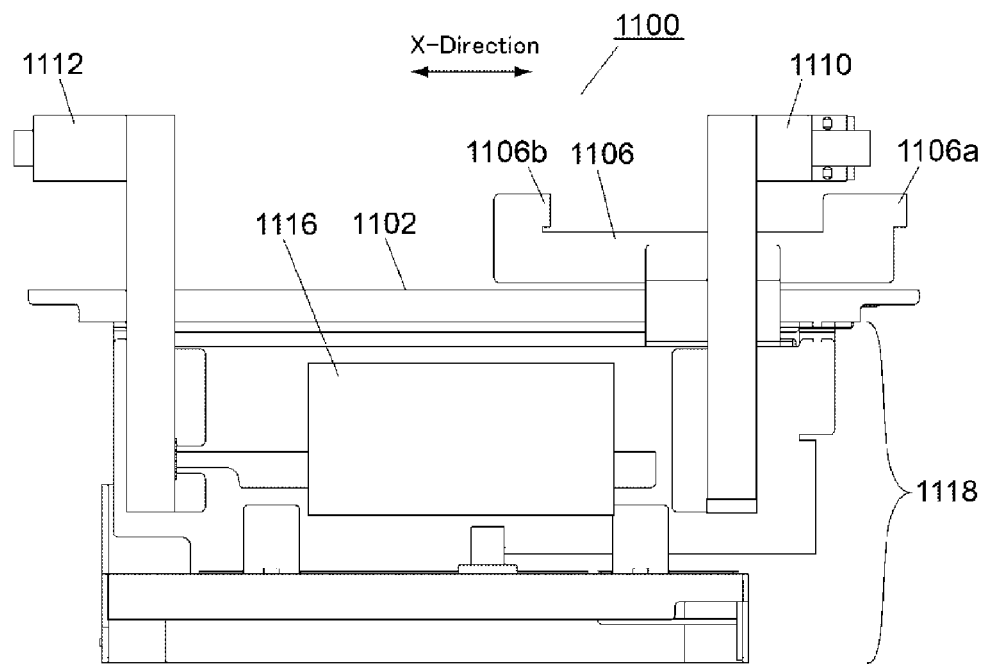
FIG. 9 is a front view of the transport mechanism.

Next, an embodiment of an automated analyzer to which the liquid collection device described above is applied will be described with reference to FIGS. 6 and 7. The liquid collection device applied in the present embodiment may be of the first embodiment or the second embodiment.

An automated analyzer 101 is configured from two automated analyzers 102a, 102b, and an inter-device transport device 112. The automated analyzers 102a, 102b are arranged next to each other in an X-direction, which is one direction on the horizontal plane, and conveyor mechanisms 106a, 106b of the respective automated analyzers 102a, 102b are linked together by the inter-device transport device 112. With the automated analyzer 101, a specimen which has been sampled at the automated analyzer 102a on the former stage side is introduced into the automated analyzer 102b on the subsequent stage side through the inter-device transport device 112, and is sampled and analyzed also at the automated analyzer 102b on the subsequent stage side.

The automated analyzer 102a on the former stage side includes an analysis operation section 104a, a conveyor mechanism 106a, and a rack introduction mechanism 118a. The conveyor mechanism 106a includes a belt conveyor 107a for conveying a specimen rack 120 holding a specimen container to one side in the X-direction (left side in FIGS. 6 and 7). The periphery of the belt conveyor 107a is covered. A specimen rack placement section 108a is provided at a beginning side of the conveyor mechanism 106a (right side in FIGS. 6 and 7), and a specimen rack recovery section 110a is provided on an end side (left side in the drawings). Covers of the specimen rack placement section 108a and the specimen rack recovery section 110a may be opened/closed, and a user is allowed to open the cover of the specimen rack placement section 108a and to place a specimen rack on the belt conveyor 107a, or to open the cover of the specimen rack recovery section 110a and to take out a specimen rack after sampling.

The rack introduction mechanism 118a moves in an Y-direction orthogonal to the X-direction on the horizontal plane, holds the specimen rack 120 on the belt conveyor 107a and introduces the same to the analysis operation section 104a side, or places the specimen rack 120 after sampling on the belt conveyor 107a.

The analysis operation section 104a is provided with a reagent accommodating section 122a, a specimen accommodating section 123a, a measurement section 124a, a sampling arm 125a, and reagent arms 127a and 129a. A plurality of reagent containers 121a containing various reagents are placed on the same circumference of the reagent accommodating section 122a. The specimen accommodating section 123a is capable of accommodating a plurality of specimen racks 120, and a specimen rack 120 introduced by the rack introduction mechanism 118a is accommodated in the specimen accommodating section 123a. The measurement section 124a includes a plurality of measurement ports (not shown), and is to optically measure the reaction inside reaction vessels disposed in the measurement ports. The reagent accommodating section 122a, the specimen accommodating section 123a, and the measurement section 124a are each a turntable that rotates on the horizontal plane, and is capable of moving a reagent container, a specimen container, or a measurement port to any position on the circumference.

The sampling arm 125a is disposed horizontally extending between the specimen accommodating section 123a and the measurement section 124a. A probe 126a for collecting a specimen is fixed at a tip end portion of the sampling arm 125a with its tip end facing vertically downward. A base end portion of the sampling arm 125a is supported by a shaft which is disposed in the vertical direction, and may rotate around the shaft and move vertically along the shaft. The probe 126a may thereby move between a position on the specimen accommodating section 123a and a position on the measurement section 124a by drawing a circular path, and be lowered from a position above a specimen container or a reaction vessel to suck in a specimen or to dispense a specimen into the reaction vessel. The sampling arm 125a and the probe 126a form a specimen collection mechanism 140a (see FIG. 12).

The reagent arms 127a and 129a are each disposed horizontally extending between the reagent accommodating section 122a and the measurement section 124a. A probe 128a for collecting a reagent is fixed to a tip end portion of the reagent arm 127a, and a probe 130a for collecting a reagent is fixed at a tip end portion of the reagent arm 128a, both probes having their tip ends facing vertically downward. Base end portions of the reagent arms 127a and 129a are each supported by a shaft which is disposed in the vertical direction, and may rotate around the shaft and move vertically along the shaft. The probes 127a and 129a may thereby move between a position on the reagent accommodating section 122a and a position on the measurement section 124a by drawing a circular path, and be lowered from a position above a reagent container to suck in a reagent and dispense the reagent into the reaction vessel. The reagent arm 127a and the probe 128a, and the reagent arm 129a and the probe 130a form independent reagent dispensing mechanisms 142a (see FIG. 12).

Additionally, in the present embodiment, the reagent dispensing mechanism 142a is formed from two reagent arms 127a and 129a, but the number of reagent arms may be one. Because two reagent arms 127a and 129a are provided, an analysis item that uses two or more reagents may be coped with.

Figure 12:
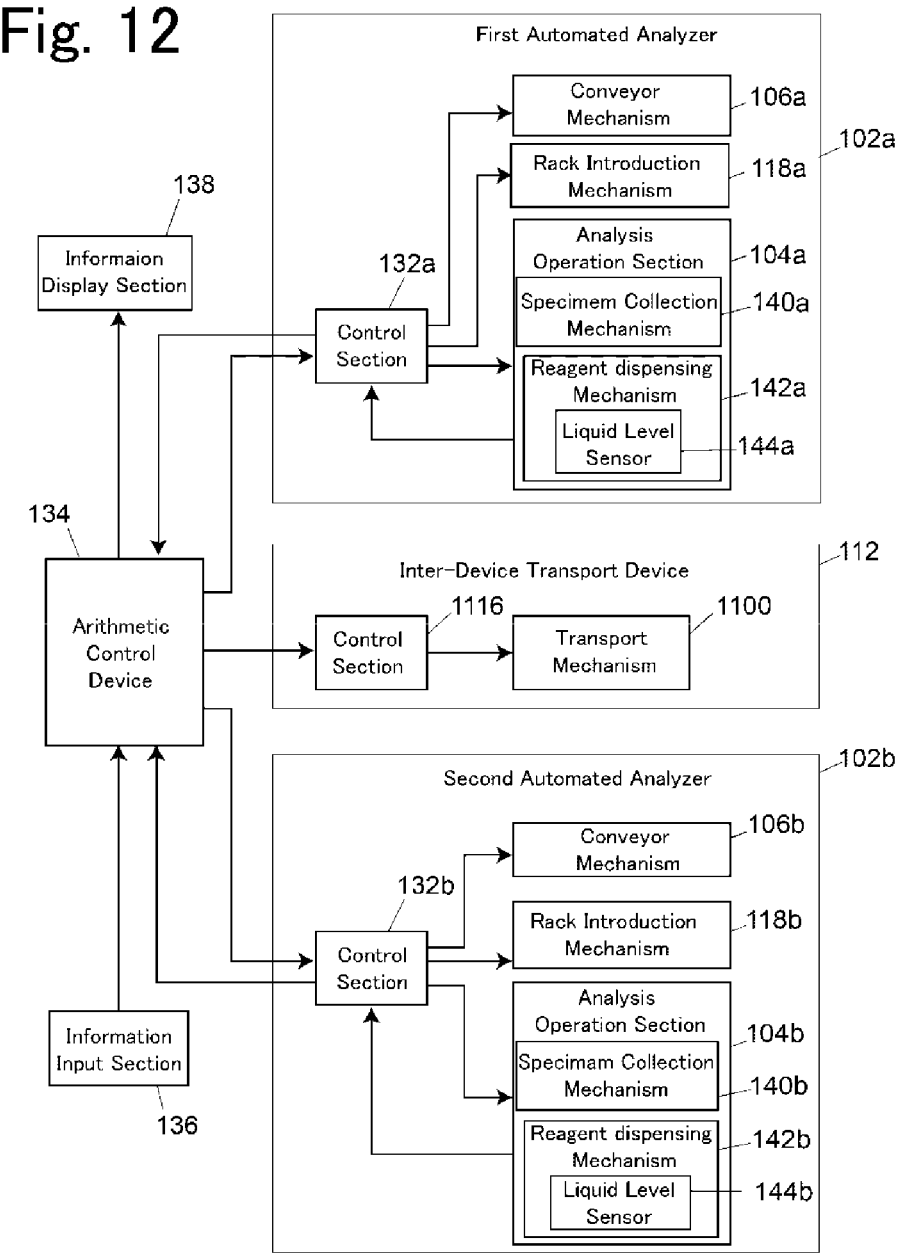
FIG. 12 is a block diagram showing a control system according to the present embodiment.

The liquid collection device according to the first embodiment or the second embodiment is applied to the reagent dispensing mechanism 142a (see FIG. 12). That is, the reagent arms 127a and 129a correspond to the arm 34 in FIG. 2, and the probes 128a and 130a correspond to the probe 2 in FIG. 2. Although not shown in FIG. 7, a liquid level sensor 144a (see FIG. 12) for detecting contact of the tip end of the probes 128a, 130a with the liquid surface is provided to the reagent dispensing mechanism 142a (see FIG. 12), and a detection signal of the liquid level sensor 144a is captured by an arithmetic control device 134 (see FIG. 12) for managing the entire automated analyzer.

The automated analyzer 102b on the subsequent stage side has the same configuration as the automated analyzer 102a on the former stage side. A beginning of a belt conveyor 107b provided to a conveyor mechanism 106b of the automated analyzer 102b and an end of the belt conveyor 107a on the former stage side are linked together by the inter-device transport device 112.

The inter-device transport device 112 includes a transport mechanism that holds the specimen rack 120 which reached the end of the belt conveyor 107a on the former stage side and places the specimen rack 120 on the beginning of the belt conveyor 107b on the subsequent stage side, and an openable cover 114 that covers the transport mechanism. Details of the transport mechanism will be given below.

An example of the transport mechanism of the inter-device transport device 112 will be described with reference to FIGS. 8 to 11.

A transport mechanism 1100 includes a table 1102 having a horizontal plane. The table 1102 is supported by a base 1118. The horizontal plane of the table 1102 is set at approximately the same height as the conveying surfaces of the belt conveyors 107a, 107b disposed at both ends. A position near an end portion, of the table 1102, at one side in the X-direction (right side in the drawing) is a transport start position 1103a at which a specimen rack which is a transport target is to be held and transport is to be started, and the belt conveyor 107a on the former stage side is disposed with its end positioned at the transport start position 1103a. A position near an end portion, of the table 1102, at the other side in the X-direction (left side in the drawing)

is a transport end position 1103b of a specimen rack, and the belt conveyor 107b on the subsequent side is disposed with its beginning positioned at the transport end position 1103b.

An arm member 1104 and an arm member 1106 extending in the X-direction are disposed, facing each other, at both side edge portions of the table 1102. The arm member 1104 and the arm member 1106 are driven at the side edge portions of the table 1102 in the X-direction and the Y-direction. With respect to the X-direction, the arm member 1104 and the arm member 1106 move together at the same time in the same direction, and with respect to the Y-direction, the arm members move together in symmetrical directions with the table 1102 at the center. Although not shown, mechanisms, such as motors, for driving the arm member 1104 and the arm member 1106 are accommodated inside the base 1118.

The arm member 1104 includes a protrusion 1104a at an end portion on the side of the transport start position 1103a, and a protrusion 1104b on the side of the transport end position 1103b. The protrusions 1104a and 1104b are for engaging with a specimen rack by being fitted in recessed sections (not shown) provided on a side surface, of the specimen rack, on the side of the arm member 1104. Movement of the arm member 1104 in the Y-direction is performed between a position at which the protrusions 1104a, 1104b are fitted in the recessed sections of the specimen rack and a position at which there is no contact with the specimen rack itself.

The arm member 1106 includes a protrusion 1106a at an end portion on the side of the transport start position 1103a, and a protrusion 1106b on the side of the transport end position 1103b. The protrusions 1106a and 1106b are for engaging with a rear surface of a specimen rack. Movement of the arm member 1106 in the Y-direction is performed between a position at which the protrusions 1106a, 1106b are engaged with the rear surface of the specimen rack and a position at which the protrusions 1106a, 1106b are not in contact with the specimen rack.

The arm members 1104 and 1106 configure handlers for holding a specimen rack and sliding and transporting the same on the table 1102 from the transport start position 1103a to the transport end position 1103b. The handler includes holding sections at two positions, on the side of the transport start position 1103a and the side of the transport end position 1103b. The holding section on the side of the transport start position 1103a is configured from the protrusion 1104a of the arm member 1104 and the protrusion 1106a on the arm member 1106, and the holding section on the side of the transport end position 1103b is configured from the protrusion 1104b of the arm member 1104 and the protrusion 1106b of the arm member 1106.

In the following, the arm member 1104 and the arm member 1106 will be collectively referred to as "handlers 1104, 1106", the holding sections of the handlers 1104, 1106 on the side of the transport start position 1103a as "first holding sections 1104a, 1106a", and the holding sections on the side of the transport end position 1103b as "second holding sections 1104b, 1106b".

The first holding sections 1104a, 1106a sandwich a specimen rack from both sides by end portions of the arm members 1104 and 1106 on the side of the transport start position 1103a to thereby fit the protrusion 1104a in the recessed section on the side surface on one side of the specimen rack, and to support the rear surface on the other side of the specimen by the protrusion 1106a. The second holding sections 1104b, 1106b sandwich the specimen rack from both sides by end portions of the arm members 1104 and 1106 on the side of the transport end position 1103b to thereby fit the protrusion 1104b in the recessed section on one side surface of the specimen rack, and to support the rear surface on the other side of the specimen by the protrusion 1106b. The handlers 1104, 1106 move in the X-direction while holding the specimen rack, and slides and transports the specimen rack on the table 1102. A guide rail 1108 to be fitted into a groove provided on a side surface of the specimen rack sliding on the table 1102 is provided at the side edge portion of the table 1102, on the side of the arm member 1106, so as to prevent the specimen rack from tipping over.

A start sensor 1110 for detecting arrival of a specimen rack at the transport start position 1103a is provided at a side of the transport start position 1103a. An end sensor 1112 for detecting arrival of a specimen rack at the transport end position 1103b is provided at a side of the transport end position 1103b. Further, a stopper 1114 for temporarily stopping, at the transport start position 1103a, a specimen rack which has been conveyed by the belt conveyor 107a on the former stage side to the transport start position 1103a is provided near the transport start position 1103a.

A circuit board 1116 is provided at a side of the base 1118. The circuit board 1116 serves as a control section (hereinafter also referred to as a control section 1116) for controlling the operation of the handlers 1104, 1106. The start sensor 1110 and the end sensor 1112 are connected to the circuit board 1116 by wires. Signals from the start sensor 1110 and the end sensor 1112 are captured by the circuit board 1116, and are used to determine starting of the transport operation of the specimen rack by the handlers 1104, 1106, and presence/absence of an error in transport of the specimen rack.

Figure 10:
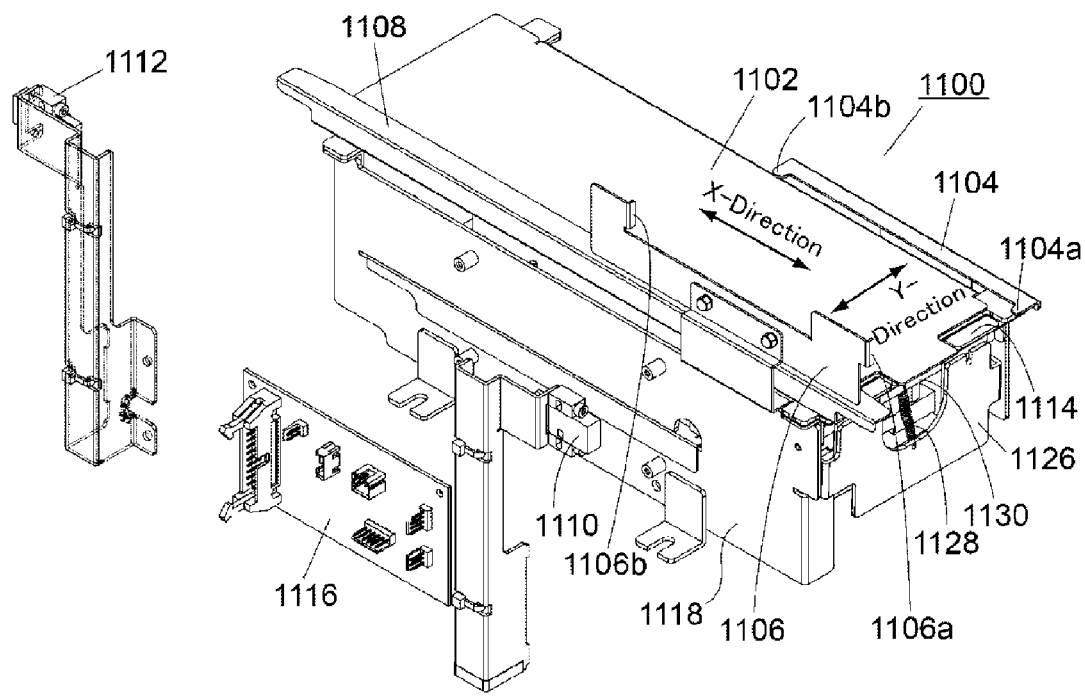
FIG. 10 is an exploded perspective view of the transport mechanism seen from obliquely above.
Figure 11:
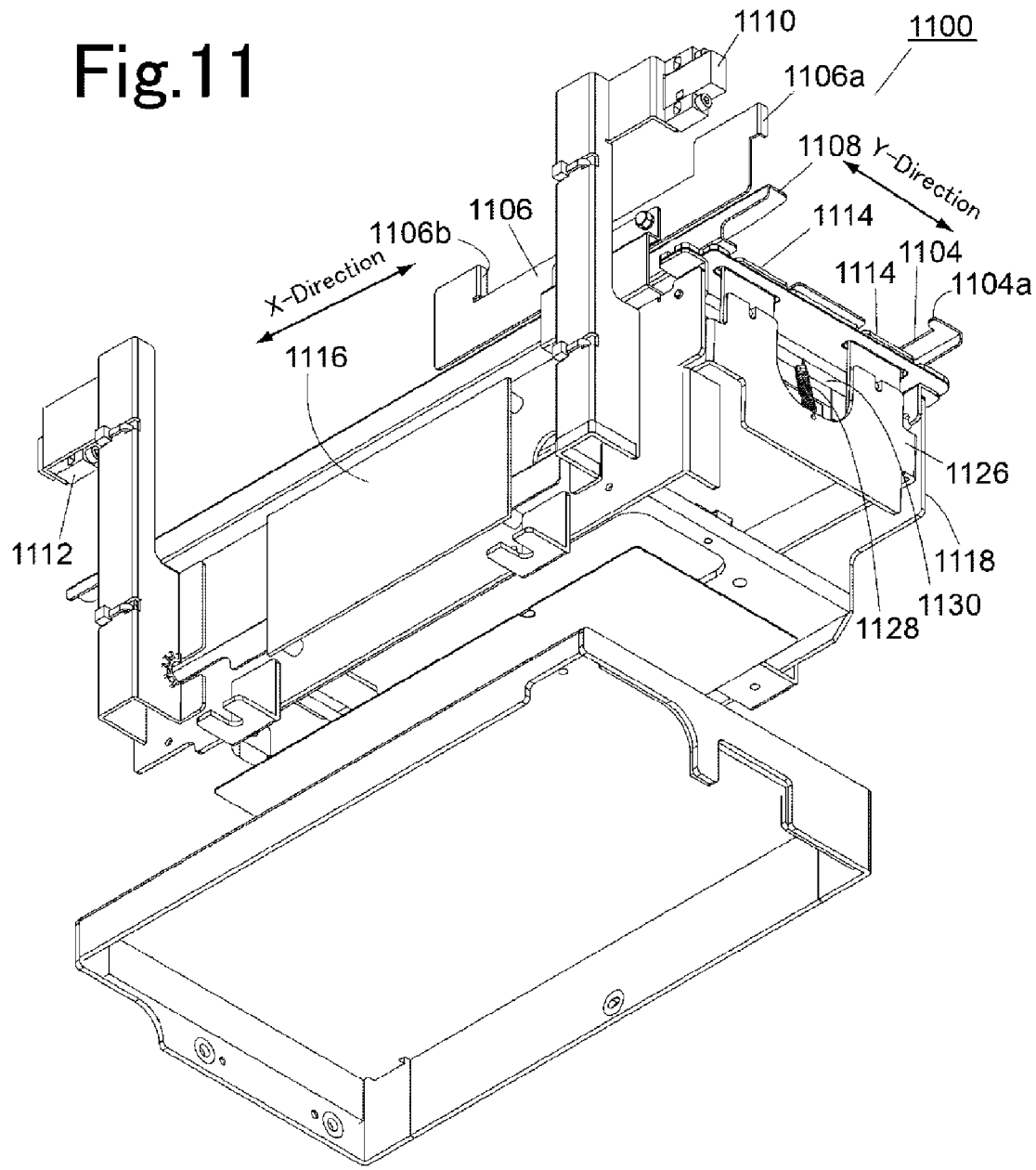
FIG. 11 is an exploded perspective view of the transport mechanism seen from obliquely below.

Additionally, in FIGS. 10 and 12, wires and modules mounted on the circuit board 1116 are omitted. In FIG. 11, some modules mounted on the circuit board 1116 are shown, but wires are omitted.

Next, a control system for the entire automated analyzer 101 will be described with reference to FIG. 12.

The first automated analyzer 102a includes a control section 132a for controlling the operation of the analysis operation section 104a, the conveyor mechanism 106a, and the rack introduction mechanism 118a, and the second automated analyzer 102b is provided with a control section 132b for controlling the operation of the analysis operation section 104b, the conveyor mechanism 106b, and the rack introduction mechanism 118b. The inter-device transport device 112 includes the control section 1116 for controlling the operation of the transport mechanism 1100.

The control sections 132a, 132b, and 1116 are each connected to the arithmetic control device 134. Measurement data obtained by the analysis operation section 104a of the first automated analyzer 102a and measurement data obtained by the analysis operation section 104b of the second automated analyzer 102b are captured by the arithmetic control device 134 through the control section 132a, and identification and quantification of a component in a specimen are performed at the arithmetic control device 134.

As described above, the analysis operation section 104a of the first automated analyzer 102a includes the specimen collection mechanism 140a and the reagent dispensing mechanism 142a. The liquid collection mechanism of the first embodiment or the second embodiment is applied to the reagent dispensing mechanism 142a, and the reagent dispensing mechanism 142a is provided with the liquid level sensor 144a for detecting that the tip end of the probes 128a, 130a has come into contact with the liquid surface. In the same manner, the analysis operation section 104b of the second automated analyzer 102b includes the specimen collection mechanism 140b and the reagent dispensing mechanism 142b, and the reagent dispensing mechanism 142b is provided with a liquid level sensor 144b for detecting that the tip end of the probes 128b, 130b has come into contact with the liquid surface. A detection signal of the liquid level sensor 144a is captured by the arithmetic control device 134 through the control section 132a, and a detection signal of the liquid level sensor 144b is captured by the arithmetic control device 134 through the control section 132b.

The arithmetic control device 134 realizes the arithmetic control device 10 of the first embodiment or the arithmetic control device 10a of the second embodiment, and an information display section 138 realizes the information display section 30 of the first embodiment or the second embodiment. The arithmetic control device 134 performs detection of foam on the liquid surface in the reagent container by using the function of detecting foam on the liquid surface, described in the first embodiment or the second embodiment, and in the case where foam is detected on the liquid surface of a reagent at the time of reagent suction, the arithmetic control device 134 performs display to this effect on the information display section 138. Then, when analysis is performed using the reagent for which foam has been detected, a warning to the effect that foam was possibly present on the liquid surface of the reagent is issued at the time of display of the analysis result on the information display section 138.

DESCRIPTION OF REFERENCE SIGNS 2, 126a, 126b, 128a, 128b, 130a, 130b: Probe
4: Pump
5: Probe driving mechanism
6: Vertical driving section
7: Rotary driving section
8, 144a, 144b: Liquid level sensor
10, 10a, 134: Arithmetic control device
12: Probe operation control means
14: Liquid level detection means
16: Post-suction liquid level calculation means
18: Difference calculation means
19: Threshold selection means
20: Foam detection means
22: Warning display means
24: Liquid level storage section
25: First threshold holding section
26, 26a: Second threshold holding section
28: Liquid information holding section
30, 138: Information display section
104a, 104b: Analysis operation section
106a, 106b: Conveyor mechanism
112: Inter-device transport device
118a, 118b: Rack introduction mechanism
120: Specimen rack
121a, 121b: Reagent container
122a, 122b: Reagent accommodating section
123a, 123b: Specimen accommodating section
124a, 124b: Measurement section
125a, 125b: Sampling arm
132a, 132b, 1116: Control section
136: Information input section
1100: Transport mechanism

The invention claimed is:

1. A liquid collection device comprising:
a probe, to be inserted from above into a container containing a liquid, for sucking in the liquid inside the container;
a probe driving mechanism for driving the probe in at least a vertical direction;
a pump for performing suction and discharge of a liquid through the probe;
a liquid level sensor for detecting that a tip end of the probe has come into contact with a liquid surface;
probe operation control means for controlling the probe driving mechanism and the pump so as to perform a probe lowering operation of lowering the probe from a position above a container containing a suction target liquid and placing the probe inside the container, and a suction operation of sucking in the liquid inside the container by a preset amount;
liquid level detection means configured to detect a liquid level before the suction operation, based on a detection signal of the liquid level sensor, by detecting a position of the probe at a time of the probe tip end coming into contact with the liquid surface at a time of the probe lowering operation;
post-suction liquid level calculation means configured to calculate a theoretical value of the liquid level after the suction operation based on the liquid level before the suction operation detected by the liquid level detection means and an amount of suction at a time of the suction operation;
a post-suction liquid level storage section for storing the theoretical value of the liquid level calculated by the post-suction liquid level calculation means;
a first threshold holding section for holding a first threshold that is set as a maximum value of an error allowed for a difference between the theoretical value of the liquid level after the suction operation calculated by the post-suction liquid level calculation means and an actual liquid level after the suction operation;
a second threshold holding section for holding a second threshold that is set greater than the first threshold;
difference calculation means configured to calculate, when the probe lowering operation is to be performed for a second or subsequent time for a container of a same suction target, a difference between the liquid level detected by the liquid level detection means and the theoretical value, for the container, of the liquid level after the suction operation stored in the post-suction liquid level storage section;
foam detection means configured to compare a difference value calculated by the difference calculation means against the first threshold and the second threshold, and to detect presence of foam if the difference value is greater than the first threshold and is equal to or smaller than the second threshold; and
warning display means configured to output to an effect that presence of foam is detected by the foam detection means, at a time of the detection, by a method allowing recognition by an operator.

2. The liquid collection device according to claim 1, wherein the second threshold is set based on a maximum value of a size of foam that is possibly generated on a liquid surface in the container.

3. The liquid collection device according to claim 2, wherein a plurality of containers containing different types of liquids that are suction target liquids of the probe are provided, and the second threshold is individually set for each type of the suction target liquid, wherein threshold selection means for selecting the second threshold according to the type of suction target liquid is further included, and
wherein the foam detection means is configured to detect presence of foam by using the second threshold selected by the threshold selection means.

4. The liquid collection device according to claim 2,
wherein a plurality of containers containing suction target liquids of the probe are provided, and the first threshold is individually set for each size or shape of the container containing the suction target liquid,
wherein threshold selection means for selecting the first threshold according to the size or the shape of the container containing the suction target liquid is further included, and
wherein the foam detection means is configured to detect presence of foam by using the first threshold selected by the threshold selection means.

5. The liquid collection device according to claim 2,
wherein a plurality of containers containing suction target liquids of the probe are provided, and the second threshold is individually set for each size or shape of the container containing the suction target liquid,
wherein threshold selection means for selecting the second threshold according to the size or the shape of the container containing the suction target liquid is further included, and
wherein the foam detection means is configured to detect presence of foam by using the second threshold selected by the threshold selection means.

6. The liquid collection device according to claim 1, wherein, when the difference value calculated by the difference calculation means is greater than the second threshold, the foam detection means detects that the container containing the suction target liquid is a new container.

7. The liquid collection device according to claim 1, further comprising:
an arithmetic control device including the probe operation control means, the liquid level detection means, the post-suction liquid level calculation means, the post-suction liquid level storage section, the threshold holding sections, the difference calculation means, and the foam detection means; and
an information display section, connected to the arithmetic control device, for displaying information held by the arithmetic control device,
wherein the warning display means is configured to display on the information display section that presence of foam is detected by the foam detection means, at a time of the detection.

8. An automated analyzer comprising:
a specimen collection mechanism for collecting a specimen from a specimen container containing the specimen, and dispensing the specimen into a reaction vessel for causing reaction of the specimen;
a reagent dispensing mechanism, configured by a liquid collection device for sucking in a reagent from a reagent container containing the reagent, and dispensing the reagent into the reaction vessel; and
a measurement section for performing measurement inside the reaction vessel containing the specimen and the reagent,
wherein the specimen collection mechanism comprising:
a probe, to be inserted from above into a container containing a liquid, for sucking in the liquid inside the container;
a probe driving mechanism for driving the probe in at least a vertical direction;
a pump for performing suction and discharge of a liquid through the probe;
a liquid level sensor for detecting that a tip end of the probe has come into contact with a liquid surface;
probe operation control means for controlling the probe driving mechanism and the pump so as to perform a probe lowering operation of lowering the probe from a position above a container containing a suction target liquid and placing the probe inside the container, and a suction operation of sucking in the liquid inside the container by a preset amount;
liquid level detection means configured to detect a liquid level before the suction operation, based on a detection signal of the liquid level sensor, by detecting a position of the probe at a time of the probe tip end coming into contact with the liquid surface at a time of the probe lowering operation;
post-suction liquid level calculation means configured to calculate a theoretical value of the liquid level after the suction operation based on the liquid level before the suction operation detected by the liquid level detection means and an amount of suction at a time of the suction operation;
a post-suction liquid level storage section for storing the theoretical value of the liquid level calculated by the post-suction liquid level calculation means;
a first threshold holding section for holding a first threshold that is set as a maximum value of an error allowed for a difference between the theoretical value of the liquid level after the suction operation calculated by the post-suction liquid level calculation means and an actual liquid level after the suction operation;
a second threshold holding section for holding a second threshold that is set greater than the first threshold;
difference calculation means configured to calculate, when the probe lowering operation is to be performed for a second or subsequent time for a container of a same suction target, a difference between the liquid level detected by the liquid level detection means and the theoretical value, for the container, of the liquid level after the suction operation stored in the post-suction liquid level storage section;
foam detection means configured to compare a difference value calculated by the difference calculation means against the first threshold and the second threshold, and to detect presence of foam if the difference value is greater than the first threshold and is equal to or smaller than the second threshold; and
warning display means configured to output to an effect that presence of foam is detected by the foam detection means, at a time of the detection, by a method allowing recognition by an operator.

9. The automated analyzer according to claim 8,
wherein a plurality of analyzers each including the specimen collection mechanism, the reagent dispensing mechanism, and the measurement section are provided, and
wherein each of the analyzers includes a belt conveyor for conveying a specimen rack holding a plurality of specimen containers in one direction, and analyzers that are disposed adjacent to each other are disposed with an end of a belt conveyor of one of the analyzers and a beginning of a belt conveyor of another of the analyzers facing each other, and the belt conveyors are linked together by an inter-device transport device including a transport mechanism for holding the specimen rack that reached the end of the belt conveyor of the one analyzer and transporting the specimen rack to the beginning of the belt conveyor of the other analyzer.

10. The automated analyzer according to claim 8,
wherein the second threshold is set based on a maximum value of a size of foam that is possibly generated on a liquid surface in the container.

11. The automated analyzer according to claim 10,
wherein a plurality of containers containing different types of liquids that are suction target liquids of the probe are provided, and the second threshold is individually set for each type of the suction target liquid,
wherein threshold selection means for selecting the second threshold according to the type of suction target liquid is further included, and
wherein the foam detection means is configured to detect presence of foam by using the second threshold selected by the threshold selection means.

12. The automated analyzer according to claim 10,
wherein a plurality of containers containing suction target liquids of the probe are provided, and the first threshold is individually set for each size or shape of the container containing the suction target liquid,
wherein threshold selection means for selecting the first threshold according to the size or the shape of the container containing the suction target liquid is further included, and
wherein the foam detection means is configured to detect presence of foam by using the first threshold selected by the threshold selection means.

13. The automated analyzer according to claim 10,
wherein a plurality of containers containing suction target liquids of the probe are provided, and the second threshold is individually set for each size or shape of the container containing the suction target liquid,
wherein threshold selection means for selecting the second threshold according to the size or the shape of the container containing the suction target liquid is further included, and
wherein the foam detection means is configured to detect presence of foam by using the second threshold selected by the threshold selection means.

14. The automated analyzer according to claim 8,
wherein, when the difference value calculated by the difference calculation means is greater than the second threshold, the foam detection means detects that the container containing the suction target liquid is a new container.

15. The automated analyzer according to claim 8,
wherein the specimen collection mechanism further comprising: an arithmetic control device including the probe operation control means, the liquid level detection means, the post-suction liquid level calculation means, the post-suction liquid level storage section, the threshold holding sections, the difference calculation means, and the foam detection means; and
an information display section, connected to the arithmetic control device, for displaying information held by the arithmetic control device,
wherein the warning display means is configured to display on the information display section that presence of foam is detected by the foam detection means, at a time of the detection.

* * * * *